United States Patent [19]

Kotwal et al.

[11] Patent Number: 5,187,268
[45] Date of Patent: Feb. 16, 1993

[54] GENE ENCODING AN ANTI-COMPLEMENT PROTEIN FROM VACCINIA

[75] Inventors: Girish Kotwal; Bernard Moss, both of Bethesda, Md.

[73] Assignee: United States of America, Washington, D.C.

[21] Appl. No.: 906,983

[22] Filed: Jul. 1, 1992

Related U.S. Application Data

[62] Division of Ser. No. 239,208, Aug. 20, 1988, Pat. No. 5,157,110.

[51] Int. Cl.⁵ .............................................. C12N 15/39
[52] U.S. Cl. ............................. 536/23.72; 435/320.1; 435/69.1; 435/235.1
[58] Field of Search .............. 536/27; 435/69.1, 320.1, 435/235.1

[56] References Cited

U.S. PATENT DOCUMENTS 5,017,482   5/1991   Stunnenberg et al. ................ 536/27

Primary Examiner—Robert J. Hill, Jr.
Assistant Examiner—Nina Ossanna
Attorney, Agent, or Firm—Townsend and Townsend

[57] ABSTRACT

A substantially pure, synthetic protein possessing anti-complement property and a DNA sequence encoding said protein are described.

2 Claims, 5 Drawing Sheets

```
     TTTTATTATTGTACGATGTCCAGGATAACATTTTTACGGATAAATAAATATGAAGGTGGAGAGCGTGACGTTCCTGACATTGTTGGGAATAGGATGCGTTCTATCATGTCTGTACTATT
       10        20        30        40        50        60        70        80        90       100       110       120
                                                       M  K  V  E  S  V  T  F  L  T  L  L  G  I  G  C  V  L  S  C  T  I
                                                                                                                    I>

P  S  R  P  I  N  M  K  E  K  N  S  V  E  T  D  A  N  A  N  Y  N  I  G  D  T  I  E  Y  L  L  P  G  Y  R  K  Q  K  M
CCGTCACGACCACCCATTAATAATGAAGGAAAATTTAAGAATTTGAAATTTAAGAATATGTGGAGACTGGAGACACTATAGATCTATGTCTACCTGGATACAGAAGCAAAAATG
       130       140       150       160       170       180       190       200       210       220       230       240

G  P  I  Y  A  K  C  T  G  T  W  T  L  F  N  Q  C  I  K  R  R  P  S  P  R  D  I  D  N  G  Q  L  D  I  G  G  V  D
GGACCTATATATGCTAAATGCTAAATGTACAGGTACTGGATGATGACACTCTTTAATCAATGTATTAAACGGAGATGCCCATCGCCTCGAGATATTGATAATGGCCAACTTGATATTGGTGGAGTAGAC
       250       260       270       280       290       300       310       320       330       340       350       360

F  G  S  S  I  T  Y  S  C  N  S  G  Y  H  L  I  G  E  S  K  S  Y  C  E  L  G  S  T  G  S  M  V  W  N  P  E  A  P  I  C
TTTGGCTCTAGTATAACGTACTCTTGTAATAGCGGATATCATTTGATCGGTGAATCGTAAATCTTATGTATGGAATCTATGGTATGGTATGGTATCTACGGAGGCACCTATTGT
       370       380       390       400       410       420       430       440       450       460       470       480

III>
 E  S  V  K  C  Q  S  P  P  S  I  S  N  G  R  H  N  G  Y  E  D  F  Y  T  D  G  S  V  V  I  Y  C  N  S  G  Y  S  L  I
GAATCTGTTAAATGCCAATCCCCTCCATCTATATCCAATGGAAGACATAACGGATACGAGGATTTTTATACCGATGGGAAGCGTTGTAACTTATAGTTGCAATAGTTGTTGATTCGTTGATT
       490       500       510       520       530       540       550       560       570       580       590       600

G  N  S  G  V  L  C  S  G  G  E  W  S  D  P  P  T  C  Q  I  V  K  C  P  H  P  T  I  S  N  G  Y  L  S  S  G  F  K  R  S
GGTAACTTCTGGGGTGTCCTGGTGTGTTCAGGAGGAGAATGGTCCGATCCACCCACGTGTCAGATTGTTAAATGTCCACACCCTACAATCTCAAATGGATACTTGTCTAGCGGGGTTTAAAGATCA
       610       620       630       640       650       660       670       680       690       700       710       720

Y  S  Y  N  D  N  V  D  F  K  C  K  Y  G  Y  K  L  S  G  S  S  S  T  C  S  P  G  N  T  W  K  P  E  L  C  V  R
TACTCATACAACGACAATGTAGACTTTAAGTGCAAGTACGGATATAAACTATCTGGTTCCTCATCATCTACTTGCTCTCCAGGAAATACATGGAAGCCGGAACTTGCAAAATGTGTACGC
       730       740       750       760       770       780       790       800       810       820       830       840
```

FIG. 2B.

GENERAL CONSENSUS SEQUENCE OF 60 AMINO ACID REPEAT SUPERFAMILY:

```
---C--P--------------Y/P-C---G------------C---G-W----A/P-C-
1                                                         60
```

```
         10        20        30        40        50        60        70        80        90
MKVESVTFLTLTLLGIGCVLSCCTIPSRPINMKFKNSVETD-ANANYNIGDTIEYLCLPGYRKQKMGPIYAKCTGTG-WTLFNQCIKRRCPSPR
                :: : :::: ......  .:::::  .:::  . ::::  :: ::: ::
         NCG-PP-P-TLSFAAPMDITLTETRFKTGTTLKYTCLPGYVRSHSTQTLT-CNSDGEWVYNTFCIYKRCRHPG
         1*                              *                                  *

100       110       120       130       140       150       160       170       180
DIDNGQLDI-GGVDFGSSITYSCNSGYHLIGESKSYCELGSTGSMVWNPEAPICESVKCQSPPSISNGRHNGYEDFYTDGSVVTYSCNSGY
 :  :::::.:  ::::::.  :::  :: ::: . :::::  :: :::::: :::::::::  :::.. ::::::  .
ELRNGQVEIKTDLSFGSQIEFSCSEGFFLIGSTTSRCEVQDRG-VGWSHPLPQCEIVCKPPPDIRNGRHSGEENFYAYGFSVTYSCDPRF
     *                        *                          *                           *

190       200       210       220       230       240       250       260
SLIGNSGVLCSG-----GEW-SDPPTCQIVKCPHPTISNGYLSSGFKRSYSYNDNVDFKCKYGYKLSGSSSSTCSPGNTWKPELPKCVR
::  .:::.. :       :  :::::::::::  :::::::: :::::::  .:..  :: .   ::::: : :::::  :: ::
SLLGHASISCTVENETIGVWRPSPPTCEKITCRKPDVSHGEMVSGFGPIYNYKDTIVFKCQKGFVLRGSSVIHCDADSKWNPSPPACEP
            *                     *                    *                            * 248
```

GENE ENCODING AN ANTI-COMPLEMENT PROTEIN FROM VACCINIA

This is a division of application Ser. No. 07/239,208, filed Aug. 20, 1988, now U.S. Pat. No. 5,157,110.

The present invention is related generally to the identification and characterization of new proteins. More particularly, the present invention is related to the identification of a gene and the encoded protein which possesses anti-complement properties. There are no known synthetic or microbial proteins capable of specifically inhibiting the complement cascade.

SUMMARY OF THE INVENTION

It is, therefore, an object of the present invention to provide substantially pure, isolated protein specifically inhibiting the complement cascade.

It is a further object of the present invention to provide a nucleotide sequence directing the synthesis of the novel protein of the present invention when cloned in a suitable expression vector.

It is another object of the present invention to provide a therapeutic composition and method for treating or controlling conditions resulting from the action of complement, by providing a synthetic inhibitor of complement.

Other objects and advantages of the present invention will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein.

DETAILED DESCRIPTION OF THE INVENTION

Figure 1A:
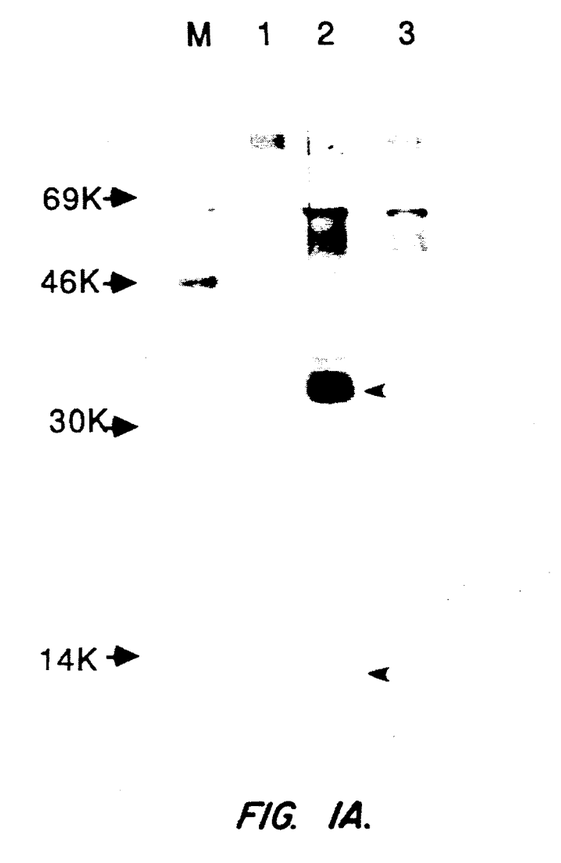
FIG. 1a shows the results of analysis of the medium from RK-13 cells infected either with standard vaccinia virus strain WR or with deletion mutant 6/2 at an moi of 50 pfu/cell in the presence of [$^{35}$S]-methionine containing minimal medium (RPMI) for 16 h, by 12.5% SDS-PAGE. Lane M has [$^{14}$C]-labeled molecular weight markers. Lanes 1 to 3 show the results of labeled medium from uninfected RK-13 cells, standard vaccinia virus infected cells and mutant 6/2 infected cells, respectively. The arrow heads indicate the two protein bands corresponding to the 35 KDa and 12 KDa proteins that are present only in the medium from the standard virus infected cells.
Figure 1B:
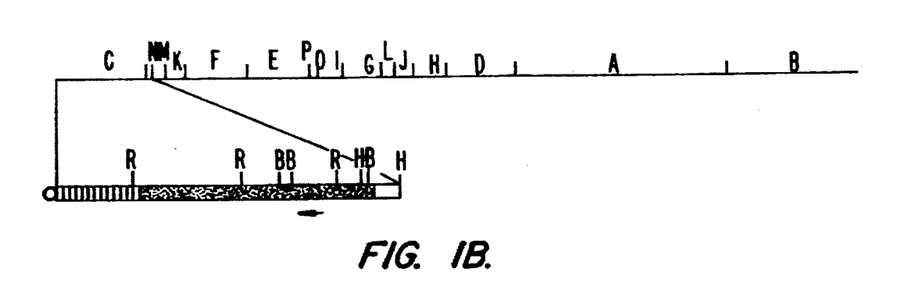
FIG. 1b shows the Hind III map of the vaccinia virus WR strain with the enlarged left end indicating the coding information absent from the genome of mutant 6/2 (the shaded area). The vertical bars indicate the inverted terminal repeats which are intact in mutant 6/2. The arrow indicates the direction and the position of the 35K protein. The fine mapping was made possible by the NH$_2$-terminal analysis of the protein and matching the sequence to that of the predicted sequence of the open reading frame as shown in FIG. 2a. The letters R, B, and H indicate the restriction sites Eco R1, Bam HI and Hind III, respectively.
Figure 2A:
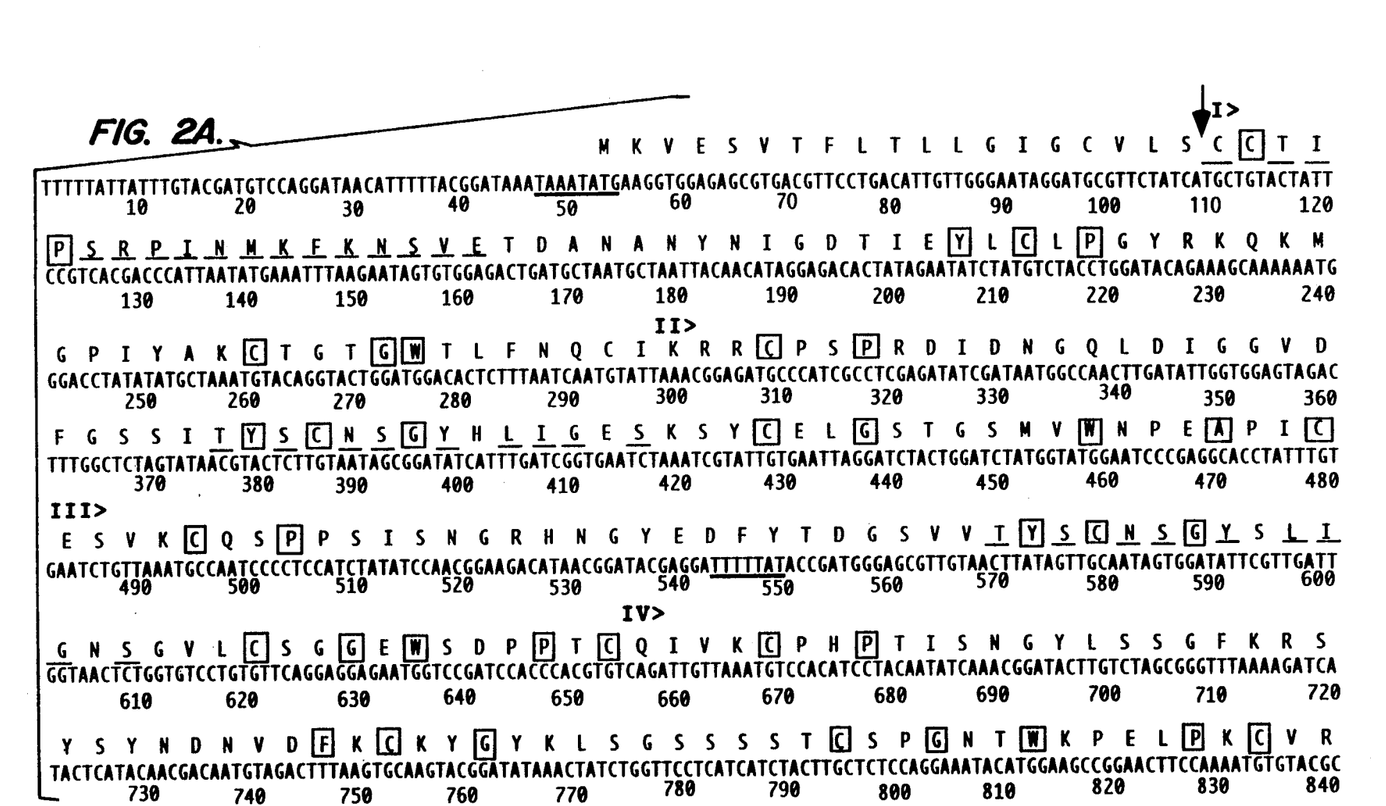
FIG. 2a shows the nucleotide sequence of the vaccinia virus (WR strain) 35K gene in 5'-3' direction. The predicted coding sequence starting at position 52 (starting codon, ATG) to position 840 (the last codon preceding the stop codon) has been translated into the corresponding amino acid sequence which is shown above the nucleotide sequence in the one letter code. The nucleotide sequence was determined on both strands by generating overlapping fragments using exonuclease III digestion and cloning them into m13 vectors and sequencing of the single strands by dideoxy-chain termination technique. The analysis was done using the Beckman microgenie program. The potential late transcription start site TAAATATG starting at nucleotide 47 has 2 extra nucleotides in comparison to the typical late transcription start site TAAATG and the potential early transcription termination signal TTTTTNT starts at nucleotide 543. NH$_2$-terminal sequence analysis of the purified 35K secretory protein by the Applied Biosystem gas-phase 477A protein sequencing system using the program version 1.5 was carried out on 35K band transferred to an Immobilon filter from a 12.5% SDS-PAGE gel. The sequence of the first 18 amino acids derived from this procedure aligned to the predicted sequence beginning with the cysteine in position 20. The underlined amino acids represent the amino acid assignments that were possible from the protein sequence. The downward arrow indicates the site at which the signal peptide is cleaved.
Figure 2B:
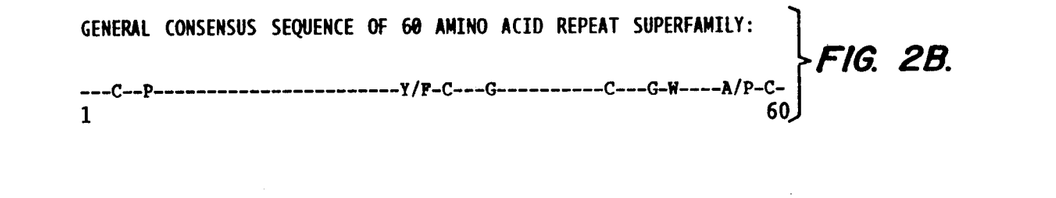
FIG. 2B: The numeral I, II, III and IV indicate the start of the 60 amino acid tandem repeating units found in the protein which have the consensus sequence shown in FIG. 2b.
Figure 3:
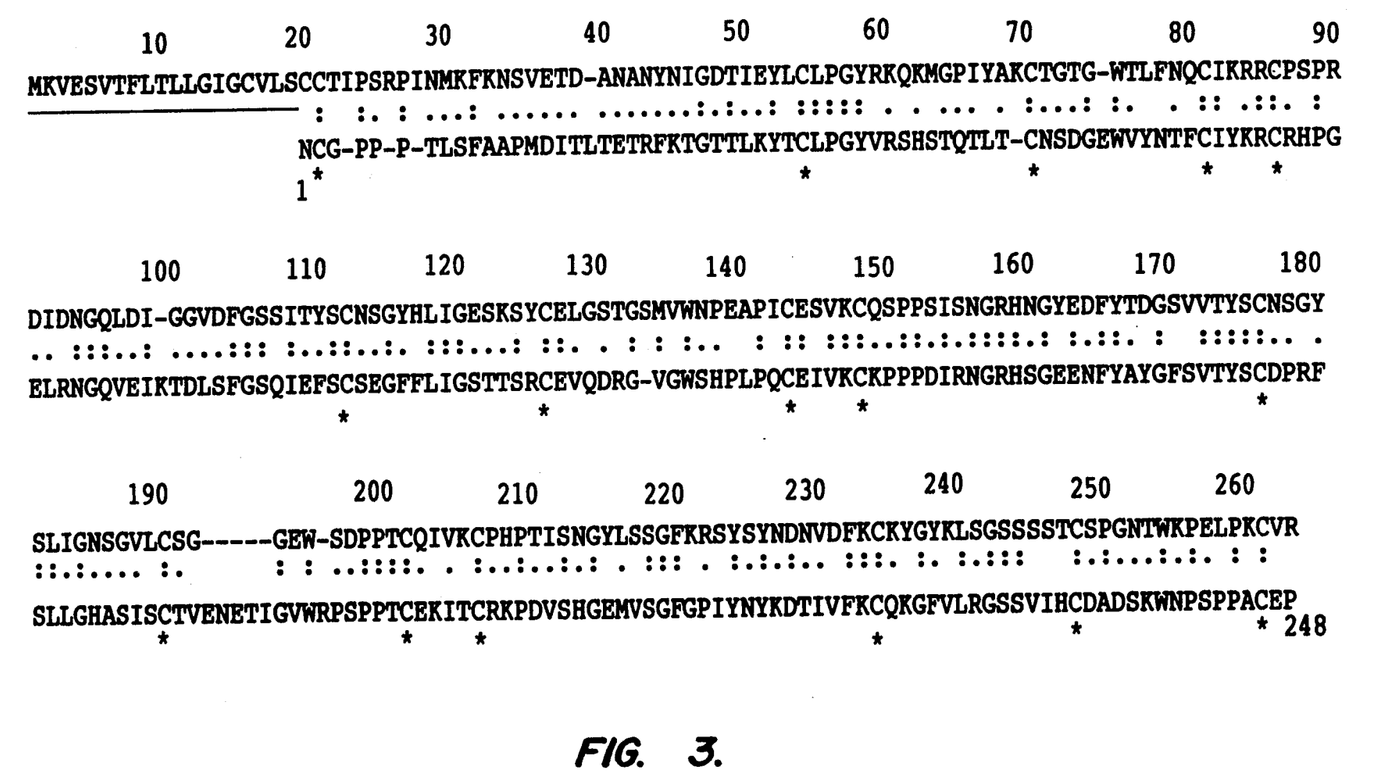
FIG. 3 shows the alignment of the deduced amino acid sequence of the vaccinia 35K secretory protein and the human C4b-binding protein. Identical amino acids are indicated by colons and conservative changes by periods. The similarity was found using the FASTP program of Lipman and Pearson searching the amino acid bank library.
Figure 4:
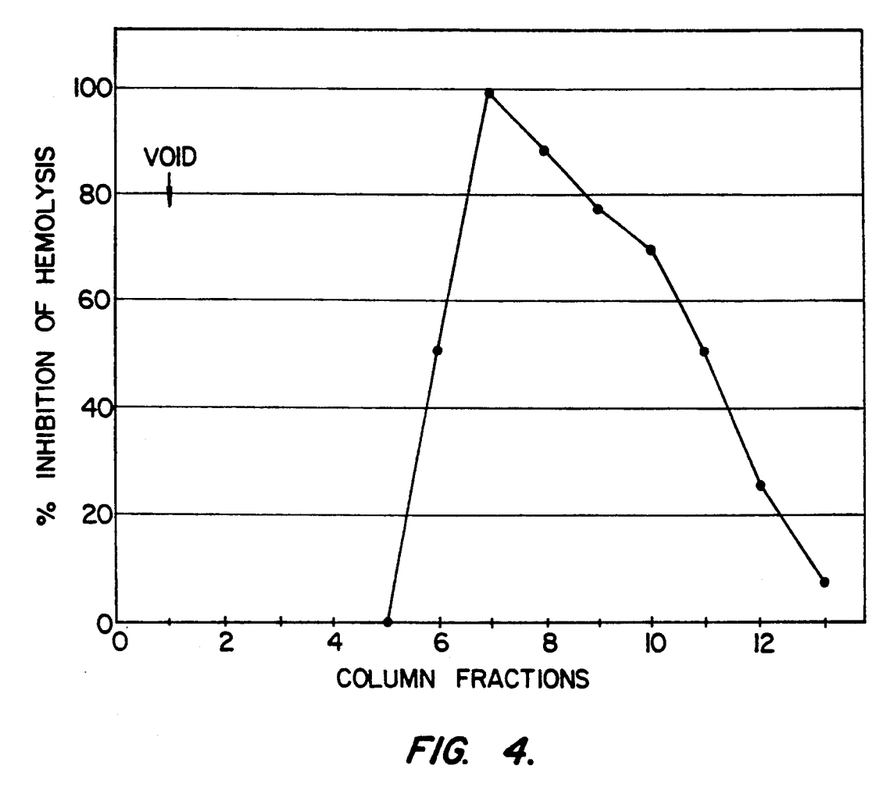
FIG. 4 shows the elution of the 35K inhibitor of complement mediated hemolysis from a G-100 Sephadex column. The void volume of the column is indicated. Individual fractions from the column were tested for inhibition of complement mediated hemolysis.
Figure 5:
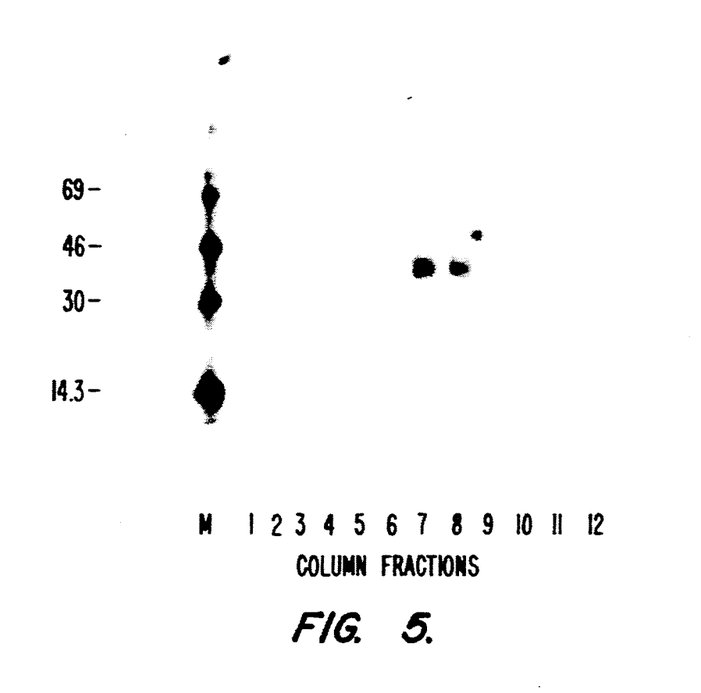
FIG. 5 shows the elution of proteins from the same G-100 Shephadex column used to measure inhibition of complement mediated hemolysis in FIG. 4. The proteins made by vaccinia virus infected RK-13 cells were metabolically labeled with [$^{35}$S]methionine and an autoradiograph is shown. The mass of marker proteins in kilodaltons is shown on the left.

The above and various other objects and advantages of the present invention are achieved by the nucleotide sequence (SEQ ID No: 1) starting with nucleotide 52 and the corresponding amino acid sequence (SEQ ID No: 2 and 3) as shown hereunder:

```
TTTTTATTATTTGTACGATGTCCAGGATAACATTTTTACGGATAAATAAATATGAAGGTG
     10        20        30        40        50        60

GAGAGCGTGACGTTCCTGACATTGTTGGGAATAGGATGCGTTCTATCATGCTGTACTATT
     70        80        90       100       110       120
```

-continued

```
CCGTCACGACCCATTAATATGAAATTTAAGAATAGTGTGGAGACTGATGCTAATGCTAAT
        130       140       150       160       170       180

TACAACATAGGAGACACTATAGAATATCTATGTCTACCTGGATACAGAAAGCAAAAAATG
        190       200       210       220       230       240

GGACCTATATATGCTAAATGTACAGGTACTGGATGGACACTCTTTAATCAATGTATTAAA
        250       260       270       280       290       300

CGGAGATGCCCATCGCCTCGAGATATCGATAATGGCCAACTTGATATTGGTGGAGTAGAC
        310       320       330       340       350       360

TTTGGCTCTAGTATAACGTACTCTTGTAATAGCGGATATCATTTGATCGGTGAATCTAAA
        370       380       390       400       410       420

TCGTATTGTGAATTAGGATCTACTGGATCTATGGTATGGAATCCCGAGGCACCTATTTGT
        430       440       450       460       470       480

GAATCTGTTAAATGCCAATCCCCTCCATCTATATCCAACGGAAGACATAACGGATACGAG
        490       500       510       520       530       540

GATTTTTATACCGATGGGAGCGTTGTAACTTATAGTTGCAATAGTGGATATTCGTTGATT
        550       560       570       580       590       600

GGTAACTCTGGTGTCCTGTGTTCAGGAGGAGAATGGTCCGATCCACCCACGTGTCAGATT
        610       620       630       640       650       660

GTTAAATGTCCACATCCTACAATATCAAACGGATACTTGTCTAGCGGGTTTAAAAGATCA
        670       680       690       700       710       720

TACTCATACAACGACAATGTAGACTTTAAGTGCAAGTACGGATATAAACTATCTGGTTCC
        730       740       750       760       770       780

TCATCATCTACTTGCTCTCCAGGAAATACATGGAAGCCGGAACTTCCAAAATGTGTACGC
        790       800       810       820       830       840
```

Amino acid sequence:

```
                                             ↓
                 1
             M K V E S V T F L T L L G I G C V L S C C T I
                                             ↑
```

SIGNAL SEQUENCE ABSENT IN THE 35K PROTEIN FOUND IN THE MEDIUM

P S R P I N M K F K N S V E T D A N A N Y N I G D T I E Y L C L P G Y R K Q K M

G P I Y A K C T G T G W T L F N Q C I K R R C P S P R D I D N G Q L D I G G V D

F G S S I T Y S C N S G Y H L I G E S K S Y C E L G S T G S M V W N P E A P I C

E S V K C Q S P P S I S N G R H N G Y E D F Y T D G S V V T Y S C N S G Y S L I

G N S G V L C S G G E W S D P P T C Q I V K C P H P T I S N G Y L S S G F K R S

Y S Y N D N V D F K C K Y G Y K L S G S S S S T C S P G N T W K P E L P K C V R

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

The term "substantially" pure as used herein means that the synthetic protein is as pure as can be obtained by employing standard, conventional purification techniques known to one of ordinary skill in the art.

The term "complement" as used herein means the complement cascade as is well known and understood by one of ordinary skill in the art and the term "anti-complement", therefore, means interfering with normal complement function.

The term "synthetic" protein as used herein means that given the amino acid sequence, the protein is synthesized by any suitable means known to one of ordinary skill in the art such as by recombinant genetic technology, chemical synthesis (e.g., by commercial polypeptide synthesizers) and the like, the method of synthesis per se not being a part of the present invention. Only as an illustration, and not as a limitation, a method of synthesizing the protein of the present invention by infection of tissue culture cells by vaccinia virus is now exemplified.

RK-13 cells (ATCC CCL 37) are grown to confluency in 150 cm² tissue culture flasks with Eagle minimal essential medium (MEM) containing 10% fetal bovine serum at 37° C. The cells are infected with vaccinia virus strain WR (ATCC VR-119) in 3 ml of MEM containing 2.5% fetal bovine serum for 2 hours. The cells monolayers are then washed extensively with serum-free medium in order to remove the inoculum and residual serum proteins. The washed cells are then overlayed with 10 ml of serum-free MEM per flask and then incubated at 37° C. for a further 20 hours. The medium is then harvested, clarified by low speed centrifugation (2,500 rev/min in an H6000A rotor in a Sorvall RC-3B centrifuge) for 10 min at 4° C. The pooled medium is then concentrated ten-fold and partially purified with an Amicon filter with a 10,000 molecular weight cut-off. The concentrate is dialyzed at 4° C. against buffer 30 mM NaCl, 10 mM EDTA, 10 mM Tris-HCl pH 8.6 using a membrane with an 8,000 molecular weight cut-off.

Further purification can be achieved by a variety of column chromatography procedures. The dialyzed material is applied to a column of DEAE Biogel that has been equilibrated with 25 mM NaCl, 5 mM EDTA, 20 mM Tris-HCl, pH 8.6 and then eluted with a gradient of 0.03 to 0.3M NaCl. Fractions are monitored by SDS polyacrylamide gel electrophoresis and those containing the 35K protein are pooled. The pooled fractions may then be applied to a Biorex 70 column that is equilibrated with 0.02M sodium phosphate buffer pH 7.2 and eluted with a gradient from 0 to 0.7M sodium chloride in 0.02M sodium phosphate. Fractions are monitored as above. Peak fractions are further purified by gel filtration using a Sephadex G-100 column equilibrated with 141 mM NaCl, 0.15 mM $CaCl_2$, 0.5 mM $MgCl_2$, 1.8 mM sodiumbarbital, 3.1 mM barbituric acid, pH 7.3-7.4.

Having obtained a substantially pure product, the specific anti-complement activity of the product is measured using standard procedures and commercially available material as follows. Sensitized sheep red blood cells (Diamedix Corporation, catalog no. 789-001) in 150 ul volumes is dispensed into the wells of a 96 microwell plate (Nunc catalog no. 1-63323). A blank is prepared by adding 50 ul of diluent (gelatin veronal buffer, Sigma catalog no. G-6514) to the first well. A reference standard is prepared by adding 5 ul of a 1:20 diluted reference serum (Diamedix Corporation, catalog no. 789-002) and 45 ul of diluent. Samples (15 ul) of purified material, 5 ul of 1:20 diluted reference serum, and 30 ul of diluent are added to the test well. The contents of the wells are mixed and the plate is then incubated at ambient temperature for 60 minutes. The contents of the well are mixed, withdrawn and centrifuged in a microcentrifuge. The supernatants are transferred to a flat bottom microwell plate and the absorbance at 415 nm is measured. Then the percent inhibition of hemolysis is calculated.

It may be further noted that proteins or compounds known to specifically block complement cascades are rare or difficult to obtain in quantity or purity. One of the few available is Cobra Venom Factor (CVF) which is a C3b binding protein, whereas the protein of the present invention is a C4b binding protein. Since the purpose and end result of both are the inhibition of the complement cascade, it is clear that the availability of the synthetic protein of the present invention avoids hunting of deadly cobras found in only restricted areas of the world or the high cost and difficulty of obtaining large amounts of plasma from animal or human sources. In addition, the vaccinia virus protein is smaller and simpler in structure than complement binding proteins previously described.

Diseases as Arthus reaction, arteritis of serum sickness and glomerulitis and proteinuria in acute nephrotoxic nephritis, hypersensitivity pneumonitis and the like, caused by different antigen sources due to abnormally high complement activity may now be treated by administering complement inhibiting amount of the purified protein of the present invention either alone or in a pharmaceutically acceptable carrier such as non-toxic buffer, physiological saline and the like. Any suitable route of administration, such as systemic or local, can be employed. The protein of the present invention can, of course, also be employed to replace CVF either in therapy or in further elucidation of the biochemical mechanisms involved in activity of the complement cascade.

A deposit of the clone has been made at the ATCC, Rockville, Md. on Aug. 19, 1988 under the accession number 67757. The deposit shall be viably maintained, replacing if it became nonviable, for a period of 30 years from the date of the deposit, or for 5 years from the last date of request for a sample of the deposit, whichever is longer, and made available to the public without restriction in accordance with the provisions of the law. The Commissioner of Patents and Trademarks, upon request, shall have access to the deposit.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A cloned gene encoding a mature protein having the amino acid sequence of SEQ ID NO:2 beginning at amino acid number 1.

2. A cloned gene of claim 1 wherein the gene has the sequence of SEQ ID NO:1 beginning at the codon encoding amino acid number 1.

* * * * *

SEQUENCE LISTING ( 1 ) GENERAL INFORMATION:

( i i i ) NUMBER OF SEQUENCES: 3

( v i ) CURRENT APPLICATION DATA:
( A ) APPLICATION NUMBER: US
( B ) FILING DATE:

( 2 ) INFORMATION FOR SEQ ID NO:1:

( i ) SEQUENCE CHARACTERISTICS:
( A ) LENGTH: 840 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
    ( A ) NAME/KEY: matpeptide
    ( B ) LOCATION: 109..840

( i x ) FEATURE:
    ( A ) NAME/KEY: sigpeptide
    ( B ) LOCATION: 52..108

( i x ) FEATURE:
    ( A ) NAME/KEY: CDS
    ( B ) LOCATION: 52..840

( x i ) SEQUENCE DESCRIPTION: SEQ ID NO:1:

```
TTTTTATTAT TTGTACGATG TCCAGGATAA CATTTTTACG GATAAAGGTG T ATG AAG        57
                                                         Met Lys
                                                         -19

GTG GAG AGC GTG ACG TTC CTG ACA TTG TTG GGA ATA GGA TGC GTT CTA       105
Val Glu Ser Val Thr Phe Leu Thr Leu Leu Gly Ile Gly Cys Val Leu
    -15                 -10                  -5

TCA TGC TGT ACT ATT CCG TCA CGA CCC ATT AAT ATG AAA TTT AAG AAT       153
Ser Cys Cys Thr Ile Pro Ser Arg Pro Ile Asn Met Lys Phe Lys Asn
     1               5                   10                  15

AGT GTG GAG ACT GAT GCT AAT GCT AAT TAC AAC ATA GGA GAC ACT ATA       201
Ser Val Glu Thr Asp Ala Asn Ala Asn Tyr Asn Ile Gly Asp Thr Ile
                 20              25                  30

GAA TAT CTA TGT CTA CCT GGA TAC AGA AAG CAA AAA ATG GGA CCT ATA       249
Glu Tyr Leu Cys Leu Pro Gly Tyr Arg Lys Gln Lys Met Gly Pro Ile
             35              40                  45

TAT GCT AAA TGT ACA GGT ACT GGA TGG ACA CTC TTT AAT CAA TGT ATT       297
Tyr Ala Lys Cys Thr Gly Thr Gly Trp Thr Leu Phe Asn Gln Cys Ile
         50              55                  60

AAA CGG AGA TGC CCA TCG CCT CGA GAT ATC GAT AAT GGC CAA CTT GAT       345
Lys Arg Arg Cys Pro Ser Pro Arg Asp Ile Asp Asn Gly Gln Leu Asp
     65              70                  75

ATT GGT GGA GTA GAC TTT GGC TCT AGT ATA ACG TAC TCT TGT AAT AGC       393
Ile Gly Gly Val Asp Phe Gly Ser Ser Ile Thr Tyr Ser Cys Asn Ser
 80              85                  90                  95

GGA TAT CAT TTG ATC GGT GAA TCT AAA TCG TAT TGT GAA TTA GGA TCT       441
Gly Tyr His Leu Ile Gly Glu Ser Lys Ser Tyr Cys Glu Leu Gly Ser
                 100                 105                 110

ACT GGA TCT ATG GTA TGG AAT CCC GAG GCA CCT ATT TGT GAA TCT GTT       489
Thr Gly Ser Met Val Trp Asn Pro Glu Ala Pro Ile Cys Glu Ser Val
             115                 120                 125

AAA TGC CAA TCC CCT CCA TCT ATA TCC AAC GGA AGA CAT AAC GGA TAC       537
Lys Cys Gln Ser Pro Pro Ser Ile Ser Asn Gly Arg His Asn Gly Tyr
         130                 135                 140

GAG GAT TTT TAT ACC GAT GGG AGC GTT GTA ACT TAT AGT TGC AAT AGT       585
Glu Asp Phe Tyr Thr Asp Gly Ser Val Val Thr Tyr Ser Cys Asn Ser
     145                 150                 155

GGA TAT TCG TTG ATT GGT AAC TCT GGT GTC CTG TGT TCA GGA GGA GAA       633
Gly Tyr Ser Leu Ile Gly Asn Ser Gly Val Leu Cys Ser Gly Gly Glu
160                 165                 170                 175

TGG TCC GAT CCA CCC ACG TGT CAG ATT GTT AAA TGT CCA CAT CCT ACA       681
Trp Ser Asp Pro Pro Thr Cys Gln Ile Val Lys Cys Pro His Pro Thr
                 180                 185                 190

ATA TCA AAC GGA TAC TTG TCT AGC GGG TTT AAA AGA TCA TAC TCA TAC       729
Ile Ser Asn Gly Tyr Leu Ser Ser Gly Phe Lys Arg Ser Tyr Ser Tyr
             195                 200                 205

AAC GAC AAT GTA GAC TTT AAG TGC AAG TAC GGA TAT AAA GTA TCT GGT       777
Asn Asp Asn Val Asp Phe Lys Cys Lys Tyr Gly Tyr Lys Val Ser Gly
         210                 215                 220

TCC TCA TCA TCT ACT TGC TCT CCA GGA AAT ACA TGG AAG CCG GAA CTT       825
Ser Ser Ser Ser Thr Cys Ser Pro Gly Asn Thr Trp Lys Pro Glu Leu
     225                 230                 235
```

```
CCA  AAA  TGT  GTA  CGC                                                                                    840
Pro  Lys  Cys  Val  Arg
240
```

( 2 ) INFORMATION FOR SEQ ID NO:2:

( i ) SEQUENCE CHARACTERISTICS:
        ( A ) LENGTH: 263 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met  Lys  Val  Glu  Ser  Val  Thr  Phe  Leu  Thr  Leu  Leu  Gly  Ile  Gly  Cys
-19            -15                       -10                             -5

Val  Leu  Ser  Cys  Cys  Thr  Ile  Pro  Ser  Arg  Pro  Ile  Asn  Met  Lys  Phe
               1              5                        10

Lys  Asn  Ser  Val  Glu  Thr  Asp  Ala  Asn  Ala  Asn  Tyr  Asn  Ile  Gly  Asp
          15             20                       25

Thr  Ile  Glu  Tyr  Leu  Cys  Leu  Pro  Gly  Tyr  Arg  Lys  Gln  Lys  Met  Gly
30                       35                  40                             45

Pro  Ile  Tyr  Ala  Lys  Cys  Thr  Gly  Thr  Gly  Trp  Thr  Leu  Phe  Asn  Gln
               50                       55                             60

Cys  Ile  Lys  Arg  Arg  Cys  Pro  Ser  Pro  Arg  Asp  Ile  Asp  Asn  Gly  Gln
               65                       70                       75

Leu  Asp  Ile  Gly  Gly  Val  Asp  Phe  Gly  Ser  Ser  Ile  Thr  Tyr  Ser  Cys
          80                       85                       90

Asn  Ser  Gly  Tyr  His  Leu  Ile  Gly  Glu  Ser  Lys  Ser  Tyr  Cys  Glu  Leu
     95                       100                      105

Gly  Ser  Thr  Gly  Ser  Met  Val  Trp  Asn  Pro  Glu  Ala  Pro  Ile  Cys  Glu
110                      115                      120                      125

Ser  Val  Lys  Cys  Gln  Ser  Pro  Pro  Ser  Ile  Ser  Asn  Gly  Arg  His  Asn
               130                      135                      140

Gly  Tyr  Glu  Asp  Phe  Tyr  Thr  Asp  Gly  Ser  Val  Val  Thr  Tyr  Ser  Cys
               145                      150                      155

Asn  Ser  Gly  Tyr  Ser  Leu  Ile  Gly  Asn  Ser  Gly  Val  Leu  Cys  Ser  Gly
          160                      165                      170

Gly  Glu  Trp  Ser  Asp  Pro  Pro  Thr  Cys  Gln  Ile  Val  Lys  Cys  Pro  His
     175                      180                      185

Pro  Thr  Ile  Ser  Asn  Gly  Tyr  Leu  Ser  Ser  Gly  Phe  Lys  Arg  Ser  Tyr
190                      195                      200                      205

Ser  Tyr  Asn  Asp  Asn  Val  Asp  Phe  Lys  Cys  Lys  Tyr  Gly  Tyr  Lys  Val
               210                      215                      220

Ser  Gly  Ser  Ser  Ser  Ser  Thr  Cys  Ser  Pro  Gly  Asn  Thr  Trp  Lys  Pro
               225                      230                      235

Glu  Leu  Pro  Lys  Cys  Val  Arg
               240
```

( 2 ) INFORMATION FOR SEQ ID NO:3:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear     ( i i ) MOLECULE TYPE: peptide     ( i x ) FEATURE:
        ( A ) NAME/KEY: Region
        ( B ) LOCATION: 1..19

( D ) OTHER INFORMATION: /note="Signal peptide"

( x i ) SEQUENCE DESCRIPTION: SEQ ID NO:3:

```
Met Lys Val Glu Ser Val Thr Phe Leu Thr Leu Leu Gly Ile Gly Cys
 1               5                  10                      15
Val Leu Ser
```